(12) United States Patent
Salgo et al.

(10) Patent No.: US 8,187,186 B2
(45) Date of Patent: May 29, 2012

(54) ULTRASONIC DIAGNOSIS OF MYOCARDIAL SYNCHRONIZATION

(75) Inventors: Ivan Salgo, Pelham, MA (US); Scott Settlemier, Marlborough, MA (US); David Prater, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1017 days.

(21) Appl. No.: 12/092,587

(22) PCT Filed: Nov. 2, 2006

(86) PCT No.: PCT/IB2006/054067
§ 371 (c)(1),
(2), (4) Date: May 5, 2008

(87) PCT Pub. No.: WO2007/054861
PCT Pub. Date: May 18, 2007

(65) Prior Publication Data
US 2008/0294048 A1    Nov. 27, 2008

Related U.S. Application Data

(60) Provisional application No. 60/734,662, filed on Nov. 8, 2005.

(51) Int. Cl.
*A61B 8/00* (2006.01)

(52) U.S. Cl. .................................. 600/438; 600/443

(58) Field of Classification Search .................. None
See application file for complete search history.

(56) References Cited

U.S. PATENT DOCUMENTS

| | | | |
|---|---|---|---|
| 5,241,473 A * | 8/1993 | Ishihara et al. | 600/443 |
| 5,533,510 A * | 7/1996 | Koch et al. | 600/443 |
| 5,622,174 A * | 4/1997 | Yamazaki | 600/441 |
| 5,718,229 A * | 2/1998 | Pesque et al. | 600/441 |
| 5,797,843 A * | 8/1998 | Fitch et al. | 600/437 |
| 5,860,927 A * | 1/1999 | Sakaguchi et al. | 600/453 |
| 6,527,717 B1 | 3/2003 | Jackson et al. | |
| 6,674,879 B1 | 1/2004 | Weisman et al. | |
| 6,863,655 B2 * | 3/2005 | Bjaerum et al. | 600/442 |
| 2002/0072670 A1 | 6/2002 | Chenal et al. | |
| 2002/0072671 A1 | 6/2002 | Chenal et al. | |
| 2003/0013964 A1 * | 1/2003 | Bjaerum et al. | 600/443 |
| 2008/0097210 A1 * | 4/2008 | Salgo et al. | 600/445 |

* cited by examiner

*Primary Examiner* — Long V. Le
*Assistant Examiner* — Angela M Hoffa
(74) *Attorney, Agent, or Firm* — W. Brinton Yorks, Jr.

(57) ABSTRACT

An ultrasonic diagnostic imaging method and system are described for detecting abnormalities in the synchronicity of heart wall stimulation. Points on opposite sides of a chamber of the heart are identified in a starting ultrasound image, then tracked through at least a portion of the heart cycle. The changing positions of lines extending between pairs of the points are accumulated and displayed in a color kinesis display in which each color depicts the location of a line at a particular point in the cardiac cycle. In an illustrated example the points are tracked through the cardiac cycle by speckle tracking of the speckle pattern of the adjacent myocardial tissue, tracking specific anatomy, or tracking tissue texture.

16 Claims, 10 Drawing Sheets

ULTRASONIC DIAGNOSIS OF MYOCARDIAL SYNCHRONIZATION

This is a continuation-in-part of pending U.S. patent application Ser. No. 11/573,214 which claims the priority of international application No. PCT/IB05/52418, filed Jul. 19, 2005 and claims the benefit of U.S. provisional patent application Ser. No. 60/600,486, filed Aug. 11, 2004.

This invention relates to ultrasonic diagnostic imaging systems and, in particular, to the use of ultrasonic imaging to diagnose electrical stimulation of the heart.

Ideally the heart should pump blood with maximum efficiency. One characteristic of a healthy heart is the uniform manner in which the heart muscle is stimulated to contract, referred to as electromechanical transduction. The heart is commanded to contract by electrochemical signals passed by sodium and potassium channels in the muscle cells of the myocardium. These signals, dispersed as they are over the entire heart muscle, should command the heart muscle cells to contract at the same instant in time. When this happens the heart contracts from a relaxed, full volume to a contracted minimal volume, thereby pumping a maximal volume of blood with each heartbeat. This is a characteristic of a healthy heart. However, when the signals that stimulate this contraction cause different regions of the heart to contract at different times, the erratic contraction will pump less than the maximal volume of blood, producing reduced efficiency and taxing the heart over time. Thus it is desirable to be able to diagnose this condition so that the necessary treatment regime, generally the implantation of a pacemaker which forces synchronous contractions, can be performed if needed. This diagnosis and its treatment is referred to as cardiac resynchronization therapy, or CRT.

Several ultrasound techniques have been proposed for CRT. All of the ultrasound techniques detect the electrical stimulation of the heart indirectly, that is, by observing the motion of the heart resulting from the stimulation. In one technique the motion of the heart wall at different locations is plotted over time, referred to as segmental sub-volumetric analysis. When the heart is being stimulated synchronously the graphical plots will appear to be symmetrical. But when a region of the heart is being stimulated later than the rest or not at all, the graphical plot from that region will be different from the others and visually distinguishable. In another approach ultrasonic tissue Doppler imaging is used to depict the heart motion in color. When the colors change nonuniformly a problem with electromechanical transduction can be inferred. This information can be presented by a parametric image which depicts regions moving in one fashion in one color and regions with dissimilar motion in another color. In yet another approach Doppler is used to depict vectors over the heart which indicate local wall motion. In a healthy heart the vectors will act and change in synchronism. However these techniques present heart motion in abstract ways that often are not intuitive to the clinician. In part this is because both time-motion and space need to be illustrated together. Accordingly it is desirable to provide an ultrasound technique for the diagnosis of heart motion synchronicity which is simple to use and intuitively understandable for the clinician.

In accordance with the principles of the present invention, an ultrasonic diagnostic apparatus and technique are provided for diagnosing the timing of stimulation of the heart muscle which is adaptable for cardiac resynchronization therapy. In the inventive method ultrasonic images of the heart are acquired over the heart cycle and the heart wall identified in at least one of the images. A series of lines are drawn across a chamber of the heart, referenced to points spaced along opposite sides of the heart. The reference points are tracked through the heart cycle and the lines displayed between the tracked points will move with the contraction and expansion of the heart. As the lines move over time, their positions are retained in the image and the buildup of depicted successive locations illustrate wall motion over the heart cycle. The line patterns are compared for uniformity to detect abnormal wall motion which may be due to asynchronous stimulation of the heart muscle.

In accordance with a further aspect of the present invention the tracked points are initially located on an automated heart wall tracing, then tracked from the speckle patterns of adjacent heart tissue. The points can also be tracked by following the movement of anatomical features or texture. In accordance with yet another aspect of the present invention the tracking of speckle patterns is done with respect to pre-scan converted ultrasound data.

In accordance with yet another aspect of the present invention the tracked points and lines can be drawn in various patterns and orientations such as an intersecting pattern crossing a short axis view of the heart or a generally orthogonal pattern of several sets of lines. The technique is applicable to different heart chambers including the left and right ventricles, and can be used with reference to both the endo- and epi-cardial borders.

Figure 1:
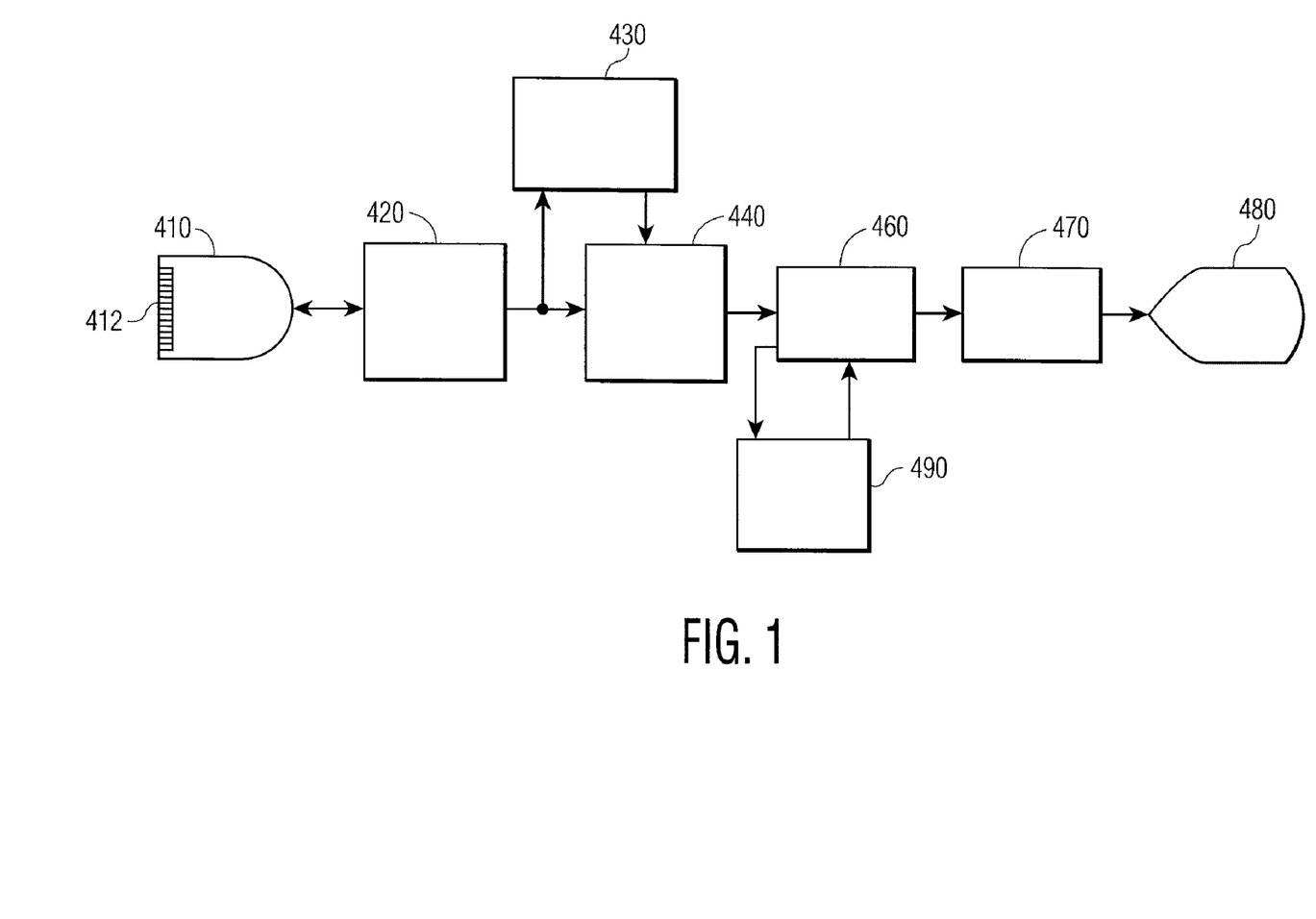
FIG. 1 illustrates in block diagram form an ultrasonic diagnostic imaging system constructed in accordance with the principles of the present invention.

Referring now to FIG. 1, a first embodiment of an ultrasonic diagnostic imaging system constructed in accordance with the principles of the present invention is shown in block diagram form. A probe or scanhead 410 which includes a one dimensional (1D) or two dimensional (2D) array 412 of transducer elements transmits ultrasonic waves and received ultrasonic echo signals. This transmission and reception is performed under control of a beamformer 420 which processes received echo signals to form coherent beams of echo signals from the anatomy being scanned. The echo information is Doppler processed by a Doppler processor 430 when Doppler information is to be presented, and the processed Doppler information is coupled to an image processor 440 which forms 2D or 3D Doppler images. For B mode imaging of tissue structure the echo signals are image processed by amplitude detection and scan converted into the desired image format for display. The images pass through a Cineloop memory 460 from which they may be coupled directly to a video processor 470 for display on an image display 480. The images may also be applied to an automatic border detection (ABD) processor 490 which operates on the 2D or 3D images to define the anatomical borders and boundaries in the images as described below. The defined borders are overlaid on the images which are coupled to the video processor 470 for display. The system may operate to define and display borders on loops of images saved in the Cineloop memory 460, or to display borders drawn on real time images produced during live scanning of a patient.

Figure 2:
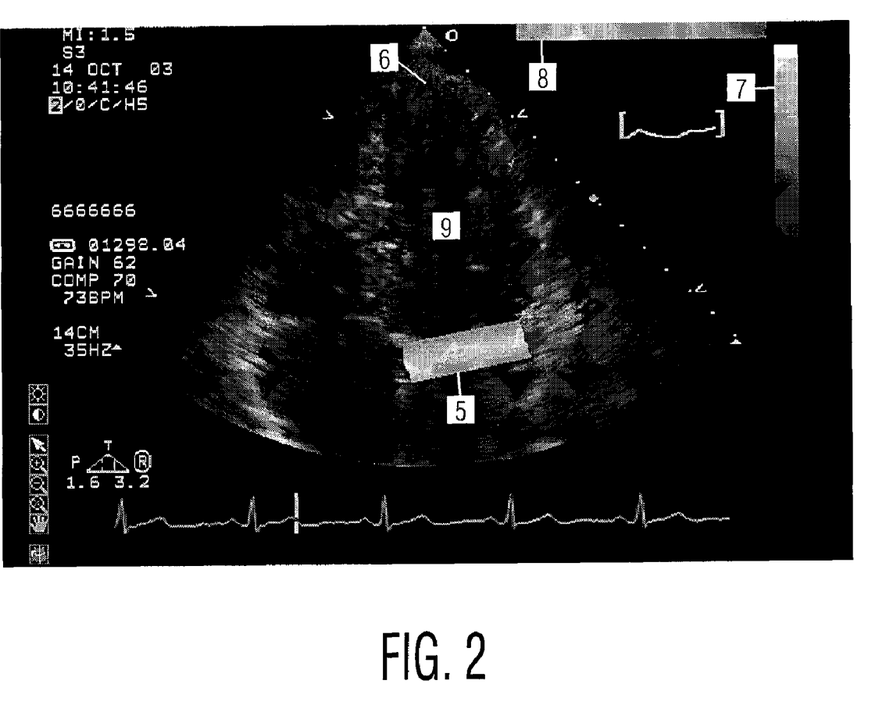
FIG. 2 is an ultrasound image of the left ventricle in which the changing locations of the mitral valve plane are depicted in gradated color shadings.

The ultrasound system of FIG. 1 can be used to produce static or live images depicting mitral annular motion as shown in FIG. 2, which is an image taken from a constructed embodiment of the present invention. Those skilled in the art will recognize the four chamber apical grayscale ultrasound image of a heart in the center of FIG. 2 which shows all four chambers of the heart in cross-section in this two dimensional image. To the right of the ultrasound image is the standard grayscale bar 7 for the image showing the range of shading used in the image. This image is acquired by a probe 410 placed below the patient's ribs and directed upward toward the apex of the heart. The reference number 9 in FIG. 2 marks the center of the LV with its apex 6 at the top of the ultrasound image. At the opposite side of the LV is the mitral valve. When the LV of a healthy heart contracts during the systolic phase of the heart cycle the myocardial walls of the LV all move smoothly and uniformly toward the center of the LV, including the side of the heart where the mitral valve is located. Thus, by this contractive action the mitral valve moves upward in the image toward the apex 6. During diastole the mitral valve moves back to its starting location as the heart muscle relaxes.

U.S. patent application Ser. No. 60/600,486, filed Aug. 11, 2004 and entitled "ULTRASONIC DIAGNOSIS OF ISCHEMIC CARDIODISEASE", the contents of which are incorporated herein by reference, describes an ultrasonic diagnostic technique in which the location of the mitral valve is tracked and depicted on the ultrasound image during the systolic phase, the diastolic phase, or both. In conventional practice physicians examine both the systolic contraction and diastolic relaxation of the heart with spectral Doppler to analyze motion of the mitral annulus, the ring of leaflet attachment in the left ventricle (LV). This analysis can be used to estimate the timing and overall motion of the LV during contraction as well as understanding the nature of constrictive and restrictive diseases of the myocardium. For example, late contraction of the LV lateral wall results in delayed excursion of the mitral annulus on that side. The diagnostic technique of the '486 application describes apparatus and a method for detecting and quantifying these motional aberrations of a diseased heart. The application describes the tracking of mitral annular motion for parametric display of mitral annular motion; use of this tracking information to map Doppler motion onto the parametric display; and to quantify both the timing and degree of excursion of mitral annular motion. In practice of the technique a sequence of images acquired during a heart cycle are analyzed to detect the mitral valve annulus as described below or by other known techniques. Preferably the position of the mitral annulus is detected rather than the valve leaflets to provide a more stable motional reference. The mitral valve location is graphically marked on an image as by a distinctive line or color stripe. This process is repeated for the next and all successive images in the sequence. Furthermore, the lines or stripes are accumulated so that each new image retains the lines or stripes identified in the previous images in the sequence and in the same locations in relation to a static reference in which they were detected. As the sequence progresses the lines or stripes build up, depicting the path of successive positions of the mitral valve during the sequence of contraction or expansion. A build-up 5 of such color stripes is shown in FIG. 2. In the actual color image from which FIG. 2 is reproduced the build-up of stripes changes hue from orange to yellow to green, in correspondence with the color bar 8 at the top of the display. The variations in hues or shadings of the color bar can be based upon various quantification metrics. For example, the mitral valve location of each successive image can be assigned a successive different hue or shade. Thus, each image frame in the sequence uses a successively different hue or shade. Alternatively, each successive hue or shade can correspond to a particular increment of motion such as 0.XX mm. In this embodiment a wide range of colors indicates a large range of motion as the spread of the line or strip build-up shows. As a third alternative, each successive hue or color can represent an increment in time during the heart cycle. Such a gradation can be synchronized to the frame acquisition times, for instance.

Each time the predetermined heart phase or phases have completed and the mitral valve motion 5 depicted for that heart cycle interval has been fully depicted, the build-up of lines or stripes is deleted until the predetermined phase starts again during a successive heart cycle. If the user decides to depict the mitral valve motion during systole the first line or stripe will be drawn at a lower position on the display and continually move upward as the heart contracts and the mitral valve moves toward the apex of the heart. If the user decides to depict mitral valve motion during diastole the lines or stripes will begin at a higher position on the display and progressively build up toward the bottom of the screen as the heart muscle relaxes and the mitral valve location moves away from the apex. If both heart phases are chosen the build-up of colors or shades will alternately move upward and then downward on the screen.

Figure 3:
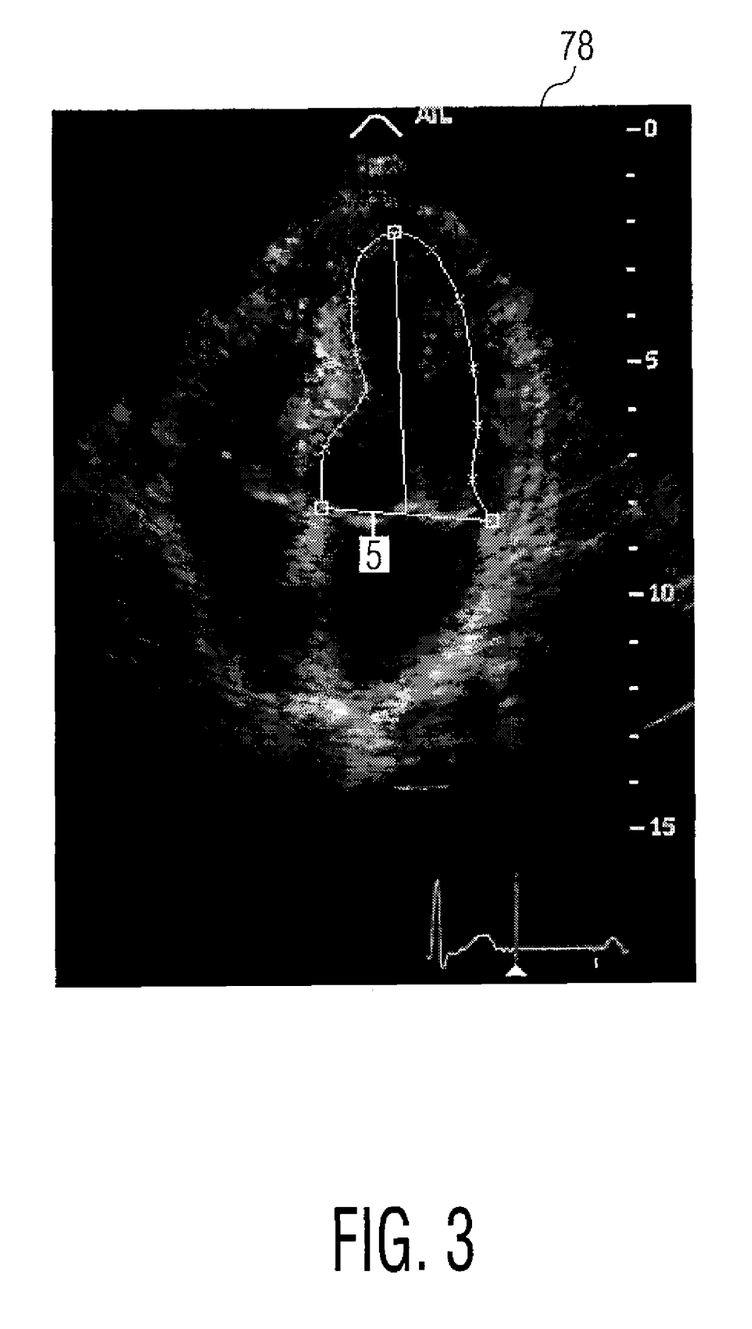
FIG. 3 illustrates an end systole image with the endocardial border drawn automatically.

Several techniques for detecting the location of the mitral valve in a heart image, a fully automated technique and an assisted automated technique, are described in the '486 application. In the automated technique the ABD processor 490 first locates two key landmarks in the image, the medial mitral annulus (MMA) and the lateral mitral annulus (LMA). This is done by doing a search of areas in the vicinity of the mitral valve plane, comparing areas or volumes of pixels with a template resembling the shapes of the LV where the mitral valve is attached to the septal and lateral walls of the LV. Filter templates defining the anticipated shapes of the MMA and LMA are cross-correlated to the pixels in the MMA and LMA search areas. When this template matching identifies the MMA and LMA in the image a line is drawn connecting the two identified points as illustrated by the line 5 in the image 78 of FIG. 3. The line 5 is colored or shaded in accordance with the gradation of a color bar for the image as previously described.

This process may be continued to identify, not only the mitral valve plane, but the complete endocardial border. The septal and lateral walls of the LV are identified by analyzing the transition in grayscale between the heart chamber and the endocardium and the angles of these walls is estimated. A line bisecting the wall angles is calculated and the apex of the LV is estimated on the bisecting line where a pixel intensity change indicates the endocardial wall at the apex. The apex is identified as the point along a line of pixels where the maximum positive brightness gradient from the LV chamber (where there are substantially no specular reflectors) to the heart wall (where many reflectors are located) is found. Once these three major landmarks of the LV have been located, the MMA, the LMA and the apex, one of a number of predetermined standard shapes for the LV is fitted to the three landmarks and the endocardial wall. When the shape has been fitted to points along the heart wall, the border tracing is smoothed and displayed over the image with a number of control or reference points located along the tracing. These reference points are shown as X's in the image 78 of FIG. 3, which also shows small squares at the MMA, LMA and apex of the traced endocardial border. The user can adjust the border manually if desired by "grabbing" a reference point with a display pointing tool such as a computer mouse or trackball and dragging the reference point to the desired location. The ABD processor 490 will then recalculate the local border segments to fit the border tracing to the newly located reference point. The technique may be repeated for other images taken during the same heart cycle, which is further aided by using the border tracing of the previous image to quickly find the border of a current image. The technique is applicable to both the endocardial and epicardial borders of the heart. Further details of this border tracing technique may be found in U.S. Pat. No. 6,491,636 (Chenal et al.)

Figure 4:
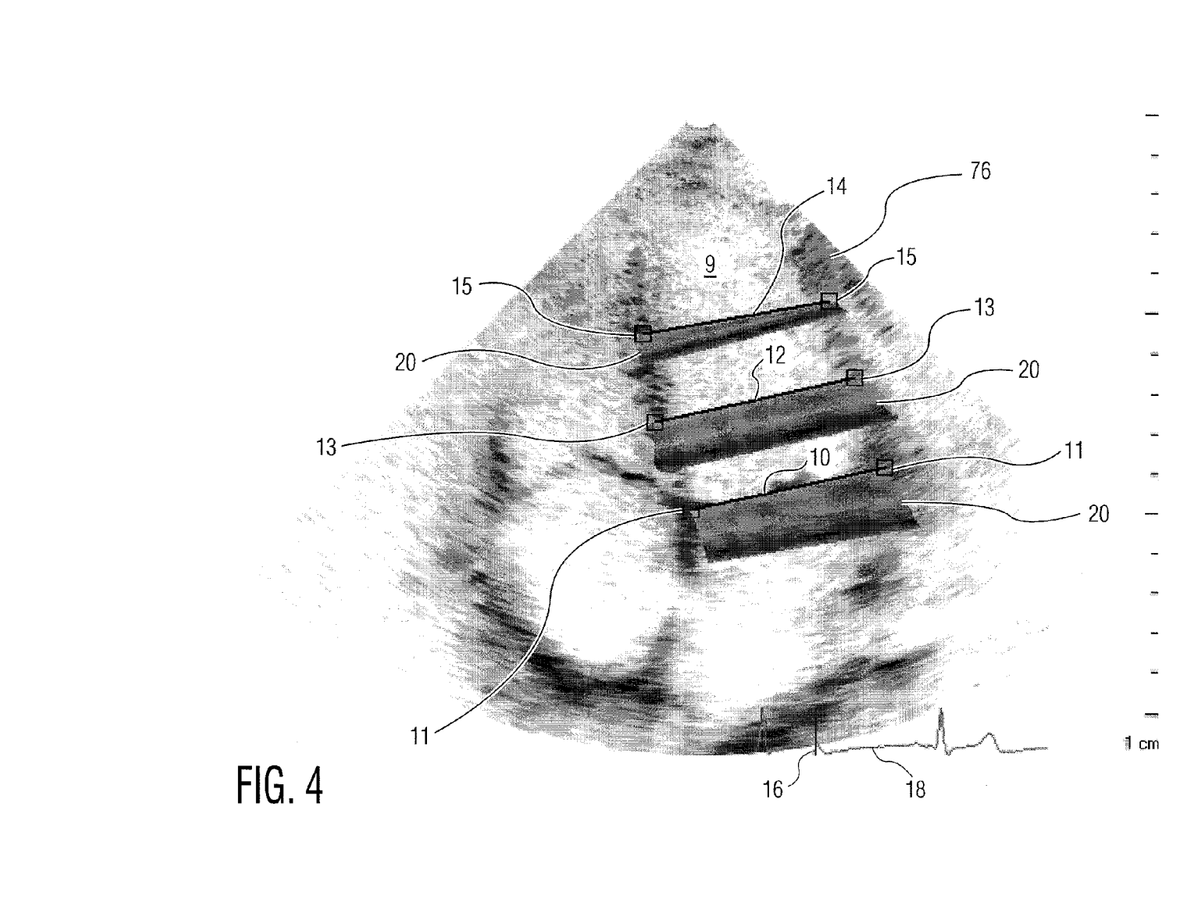
FIG. 4 illustrates a plurality of color kinesis bands between pairs of reference points on opposite sides of the left ventricle in accordance with the principles of the present invention.

In accordance with the principles of the present invention the mitral valve color kinesis technique shown in FIG. 2 is extended to simultaneously illustrate motional effects at a plurality of regions of the heart, enabling the clinician to effectively diagnose possible cardiac synchronization problems over the heart chamber. FIG. 4 illustrates an image 76 produced in accordance with the present invention. In this example three lines 10, 12, and 14 are shown extending across the LV 9 of the image. These lines are connected between reference point pairs 11, 13, 15 located on opposite sides of the LV. The reference points are located on the same locations of the endocardium or myocardium through the heart cycle and the lines 10, 12, and 14 between them are continually drawn and accumulated in changing shades or colors as described for the mitral valve above. The lines in FIG. 4 connect the reference point pairs 11, 13, 15 as they are shown at the instant of the image 76, which is subsequent to an end diastole starting point as shown by time marker 16 on the ECG trace 18 at the bottom of the image. Thus, the accumulated bands of color kinesis 20 show the progression of positions of the lines 10, 12, 14 over the heart cycle from end diastole to the later time of image 76. If the walls of the heart are moving in synchronism the color kinesis bands 20 should be relatively symmetrical trapezoids. In this image it is seen that the two lower bands are approximately symmetrical but that the upper band between reference points 15 is asymmetrical with lesser movement at the lateral wall on the right side of the image. The clinician my therefore want to conduct more detailed diagnosis of this region of the heart.

Figure 5:
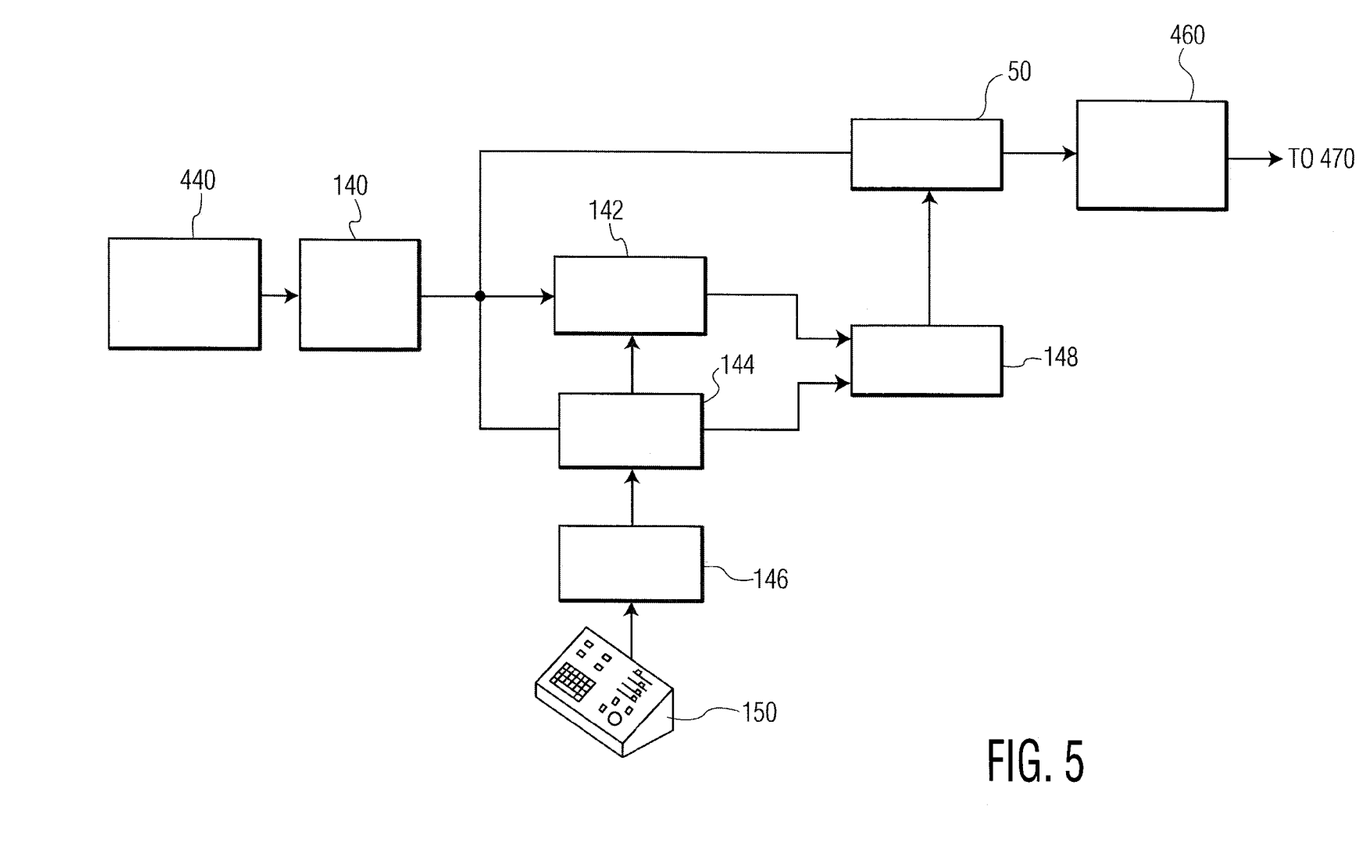
FIG. 5 illustrates in block diagram form a portion of the ultrasound system of FIG. 1 constructed in accordance with the principles of the present invention.

An ultrasound system constructed to produce images such as that of FIG. 4 is shown in FIG. 5, which is a detailed block diagram of the portion of the ultrasound system between the image processor 440 and the video processor 470 of FIG. 1. The image processor 440 produces scanline data of an image which is stored in image data memory 140. A first, starting point image is analyzed by border detection of a heart chamber by an ABD processor 144 as described above and the lines 10, 12, and 14 drawn over the mitral valve plane as described above and between pairs of control or reference points. The illustrated reference points 11, 13, 15 and lines 10, 12, 14 are produced by a graphics processor 148 for overlay over a planar or volumetric image. The image with its graphic overlay are converted to the desired display format by a scan converter 50 and stored in a Cineloop memory 460. The image such as the one shown in FIG. 4 is then coupled to the video processor 470 for display.

The lines 10, 12, 14 for successive images can be drawn between the control or reference points on the borders of the successive images. However, in a constructed embodiment, the lines of successive images are drawn between points 11, 13, 15 located on successive images by tracking the starting anatomical positions by the speckle pattern produced by the local tissue. The locations of the reference points 11, 13, 15 in the initial image (e.g., end diastole image) are coupled from the ABD processor 144 to a speckle tracker 142, which identifies regions of pixels around the reference points in the adjacent myocardium. The speckle patterns of these pixels is saved and compared with speckle patterns in the same regions of the successive images and the speckle patterns matched by block matching. The difficulty and precision of the matching is determined by setting a correlation coefficient for the matching. The reference point locations in the images are thus tracked from image to image by following the speckle patterns around the points. When the speckle tracker 142 locates the reference points 11, 13, 15 in a new image the reference point locations are coupled to the graphics processor 148, the color lines produced and accumulated with the previously determined lines and a graphic overlay produced for the new image. The new image and its graphic overlay are scan converted and displayed on an image display which will produce an image such as image 76 of FIG. 4. The clinician can use the displayed motional information to identify problems of cardiac motion and synchronicity.

Instead of tracking the speckle pattern of the myocardial tissue surrounding, underlying, or adjacent to the reference points, it may be appreciated that the reference point locations may be tracked by means other than speckle tracking, that is, by tracking image characteristics which are greater than a wavelength in size. For instance, the movement of specific anatomical features may be tracked. As another example, tissue texture may be tracked. It will also be appreciated that the targeted characteristics may be tracked in either pre-scan converted or post-scan converted image data.

Figure 6:
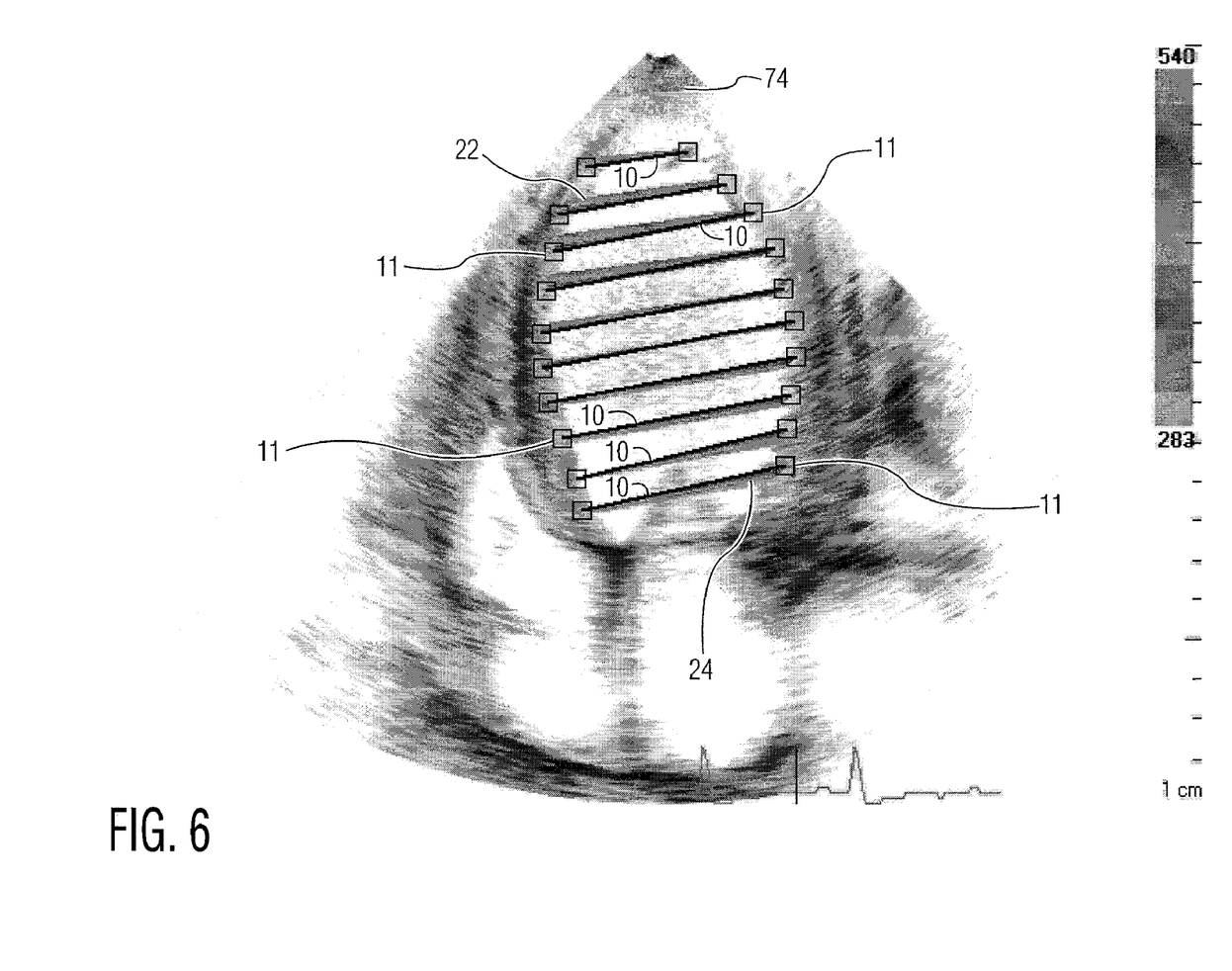
FIG. 6 is an example of an ultrasound image produced in accordance with the present invention and depicting abnormal wall motion.

FIG. 6 illustrates another image 74 produced in accordance with the principles of the present invention. In this example the clinician has elected to use ten pairs of reference points, which is done by selecting ten pairs from the control panel 150 of the ultrasound system in FIG. 5. This reference point data is stored at 146 and applied to the ABD processor 144 and speckle tracker 142, which set the number of pairs of reference points in the initial image and track the points through subsequent images. The reference points are by default distributed at uniformly spaced distances along the heart border, but the positions can also be adjusted manually by the clinician by pointing and dragging as discussed above. The example of FIG. 6 illustrates abnormal wall motion and possible synchronization problems. The color kinesis band 22 near the apex of the heart is seen to have very little height on the right side, resulting from little motion of the lateral wall of the heart at that location. The color kinesis band 24 near the mitral valve is seen to have only a very slight excursion at the septal wall on the left side of the heart chamber. This heart may thus be a candidate for more extensive diagnosis and analysis.

Figure 7:
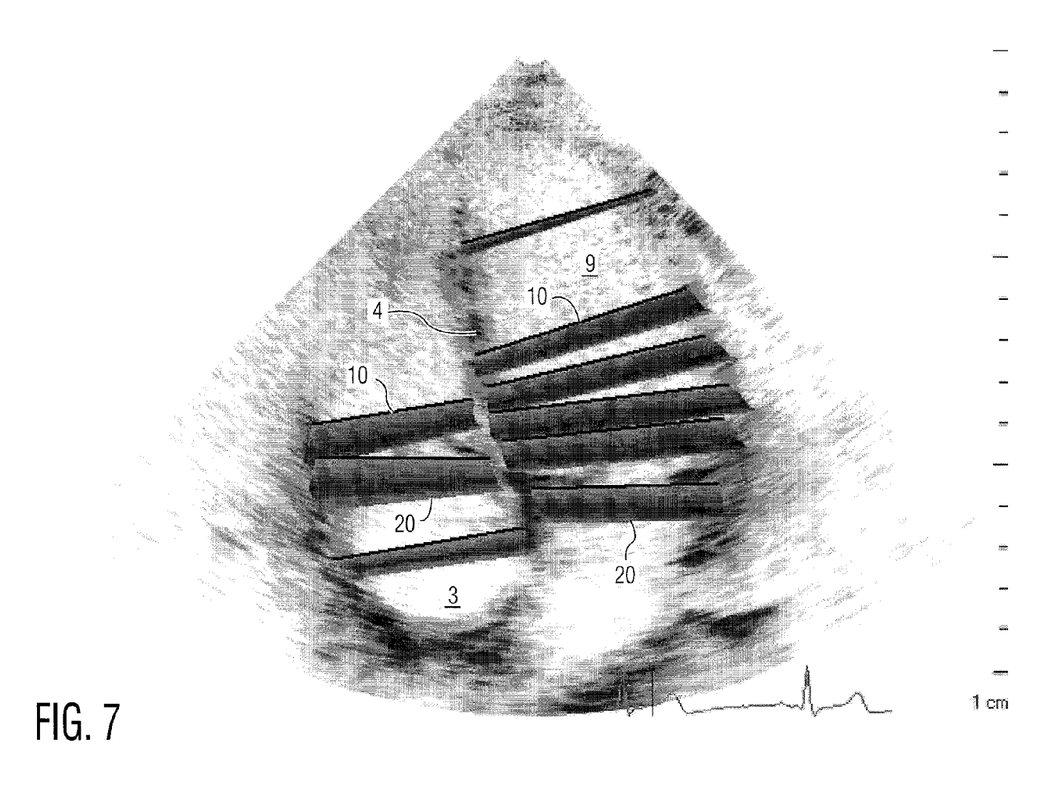
FIG. 7 is an example of an ultrasound image produced in accordance with the present invention showing color kinesis bands across both the left and right ventricles.

The diagnostic tools of the present invention can be used for other chambers of the heart such as the right ventricle (RV) 3 as illustrated in the example of FIG. 7. In this example the color kinesis bands 20 reveal greater lateral motion of the RV as compared to the motion of the septum 4.

Figure 8:
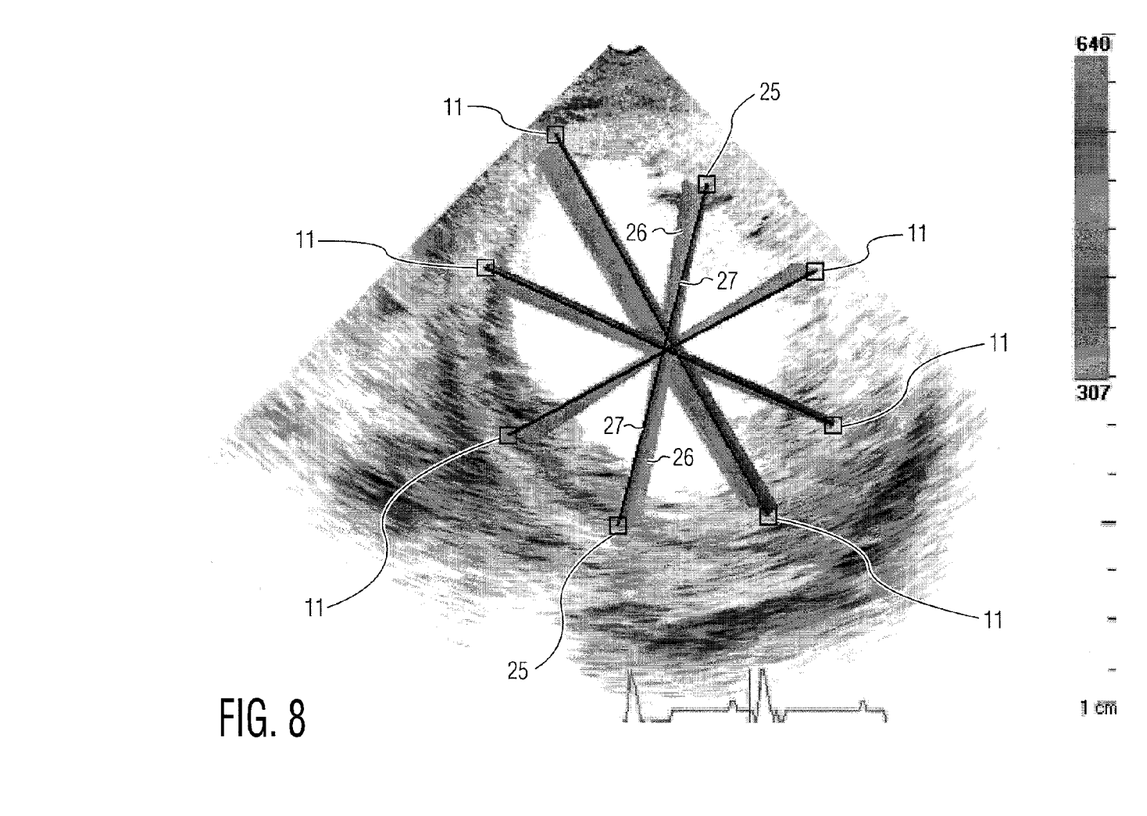
FIG. 8 is an example of an ultrasound image produced in accordance with the present invention showing color kinesis bands extending across a transverse (short axis) image of a heart chamber.

The diagnostic tools of the present invention are applicable to transverse views of the heart in addition to the previously illustrated longitudinal views. FIG. 8 is a transverse view across the left ventricle 9 with the reference points 11 dispersed around the perimeter of the heart chamber. The lines 10 are drawn between pairs of points 11 as the locations of the points are followed by speckle tracking over the heart cycle. The positions of the lines 10 are accumulated as color kinesis bands 20. The positions of the bands with reference to the lines, such as band 26 with respect to line 27 between points 25, show a twisting motion of the heart. Since the heart is approximately a helically wound bundle of muscle fibers, there is a distinct twist to its motion as it beats, which is revealed in the example of FIG. 8.

Figure 9:
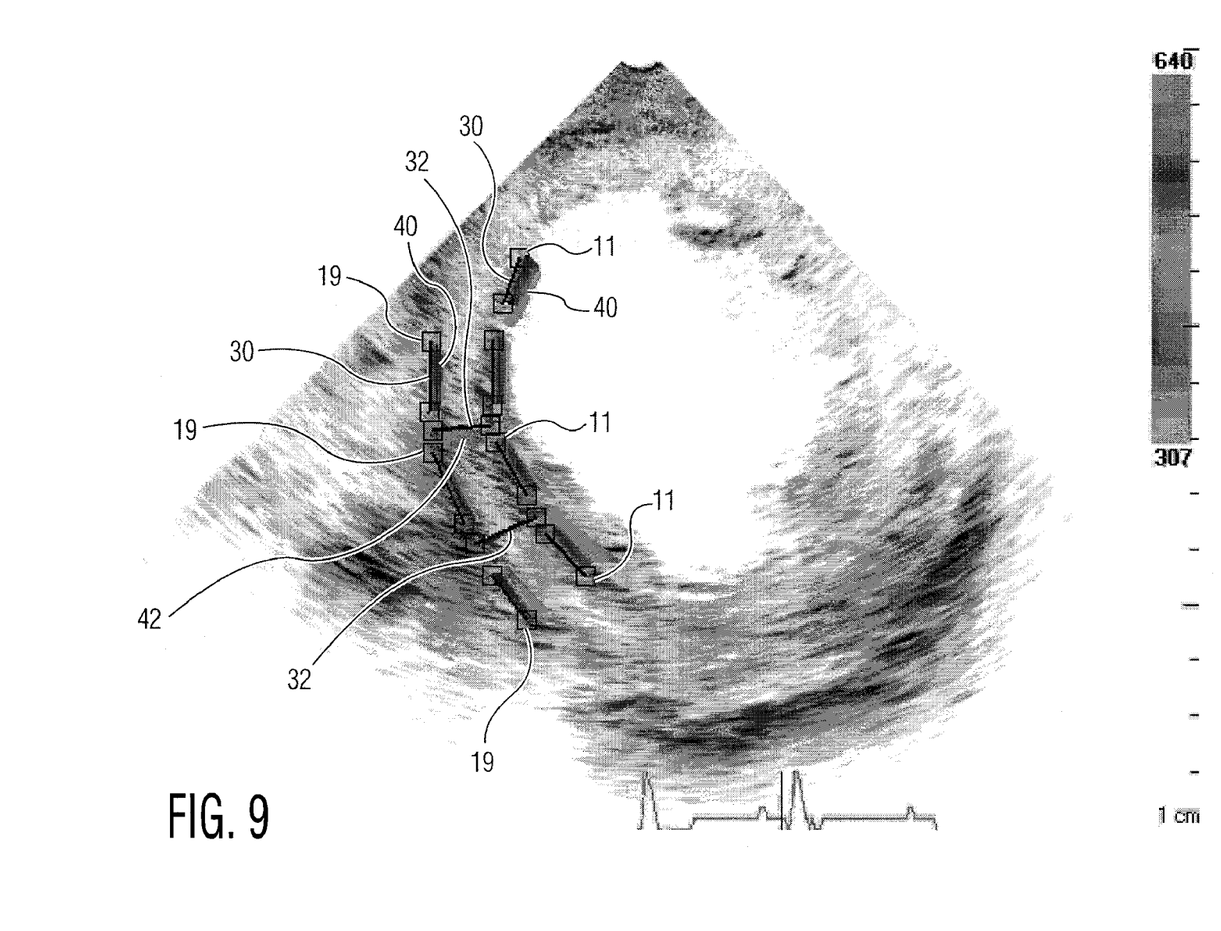
FIG. 9 is an example of an ultrasound image produced in accordance with the present invention showing color kinesis bands along and between the endocardial wall and the epi-cardial wall.

FIG. 9 is an example of an image of the present invention in which reference points 11 are located along the endocardium and reference points 19 are located along the epicardium in the same transverse image of the heart. Lines 30 are drawn and their changing positions represented in color kinesis bands 30 along the endocardial and epicardial borders in the image. In addition, lines 32 are drawn across the myocardium and tracked as bands 42 in the image. Thus, the motion of several parts of the heart anatomy is tracked in different directions at the same time.

Figure 10:
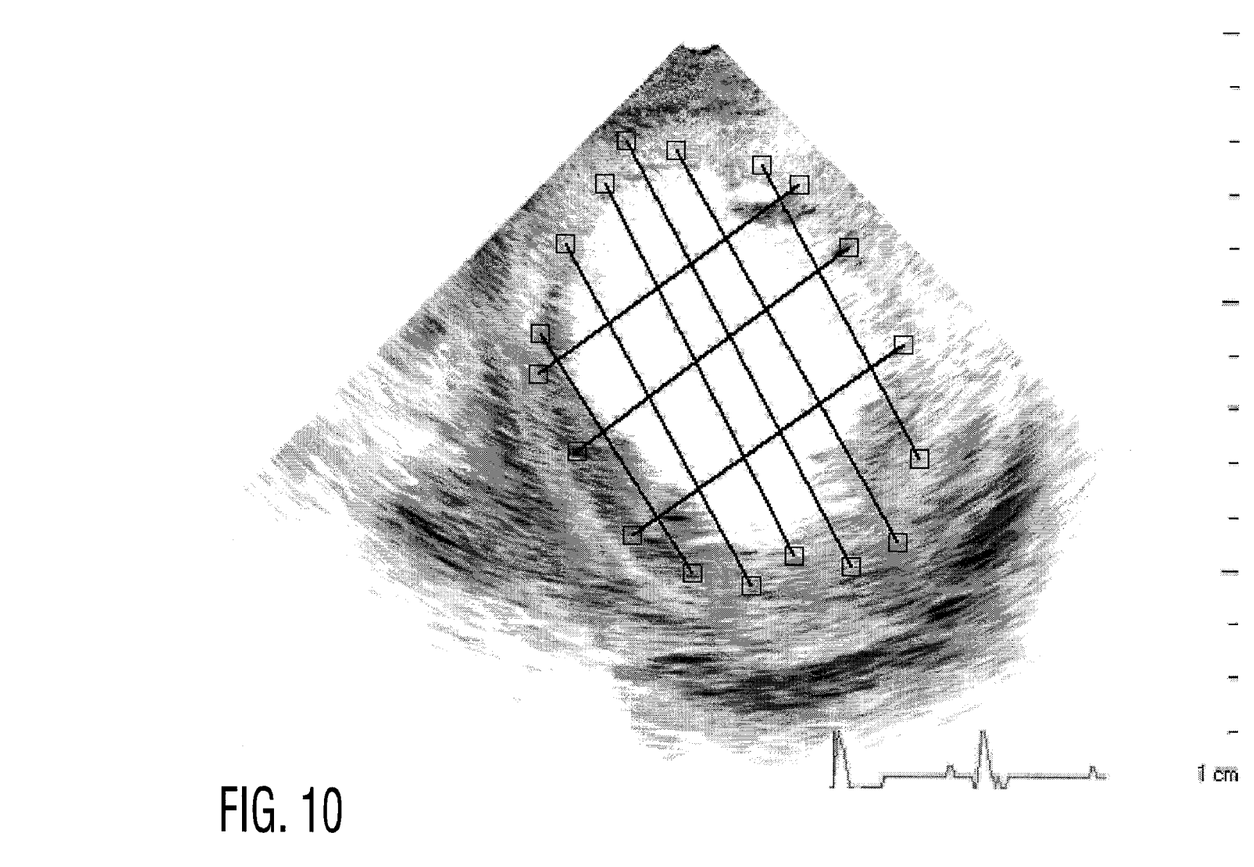
FIG. 10 is an example of an ultrasound image produced in accordance with the present invention showing lines drawn in orthogonal directions between pairs of heart chamber wall reference points.

FIG. 10 is another example of the tracking of motion in different directions in the same image. In this example lines 60 are drawn in approximately parallel orientations between one set of reference points 61 and another group of lines 64 are drawn between reference points 65. Motion of the myocardium in approximately orthogonal directions is thus depicted in the same image.

It will also be apparent to those skilled in the art that quantified numerical measures or representations of the excursions of lines between reference points can be derived from the color coding or spacing of the successive line locations. Both heart wall positions and rates of change in position (derivatives of positional change or velocity) can be displayed to assist in the diagnosis. The presentation of color kinesis bands at different locations across the chamber enables the clinician to make comparative diagnoses of the motion at different locations in the chamber. It will be appreciated that the techniques of the present invention are also applicable to three dimensional images, in which the lines can appear as surfaces and the color kinesis bands as 3D regions of color-depicted locational change. In order to enable the clinician to see both the anatomy and the motion of the reference points, the volumes formed by the accumulation of surfaces during the heart cycle may be display semi-transparently so that the clinician can visualize anatomy behind the colored volumes.

It will be appreciated that, instead of or in addition to showing the motion of the heart wall in a color or shaded representation, the motion may also be indicated in a quantified form. Motion may be indicated numerically in distance or velocity units and the direction (vector) of the motion may be displayed.

Variations of the examples described above are also within the scope of the present invention. For instance, instead of identifying the starting locations of the reference points through automated or semi-automated border detection, the points can be placed manually on the starting image by the clinician using a pointing device such as a computer mouse or trackball. The selected tracking method (speckle, feature, texture or other) may then be used to track the locations of the manually placed reference points through the sequence of images.

What is claimed:

1. A method for depicting the synchronous functioning of the heart from a sequence of images acquired during a plurality of phases of the heart cycle comprising:
   acquiring a sequence of ultrasound images of the heart with an ultrasound imaging system during a sequence of phases of the heart cycle;
   identifying in each image of the sequence the locations of reference points on opposite sides of a chamber of the heart;
   connecting a pair of reference points on opposite sides of the chamber with a line extending across the chamber of the heart;
   tracking the reference points and the connecting line during the sequence of phases of the heart cycle;
   accumulating positional changes of the line in the same locations in relation to a static reference in which the line was first detected during the sequence of phases of the heart cycle; and
   displaying the shape of the accumulated changes of the positions of the line at the end of the sequence of phases of the heart cycle as an indicator of asynchronicity.

2. The method of claim 1, wherein connecting further comprises producing a plurality of lines between different pairs of reference points on opposite sides of the heart chamber; and further comprising:
   accumulating positional changes of the lines in the same locations in relation to a static reference in which the lines were first detected during the sequence of phases of the heart cycle,
   wherein displaying further comprises displaying the shape of the accumulated changes of the positions of the lines at the end of the sequence of phases of the heart cycle as an indicator of asynchronicity.

3. The method of claim 2, wherein displaying further comprises displaying the accumulated changes of the positions of the lines in different colors.

4. The method of claim 3, wherein acquiring comprises acquiring a sequence of three dimensional images of the heart,
   wherein the lines appear as surfaces.

5. The method of claim 1, wherein tracking further comprises tracking the reference points during the sequence of phases of the heart cycle by speckle tracking.

6. The method of claim 5, wherein speckle tracking further comprises tracking the speckle pattern of myocardial tissue located in the vicinity of the reference points from one image to another.

7. The method of claim 1, wherein tracking further comprises tracking the reference points during the selected phase or phases of the heart cycle by automated border detection of successive heart images.

8. An ultrasonic diagnostic imaging system for diagnosing the synchronicity of cardiac motion comprising:
   an ultrasound probe;
   an image processor;
   a border detector configured to identify points on opposite sides of a heart chamber in an ultrasound image;
   a speckle tracker configured to track the changes in the positions of the points during at least a portion of a cardiac cycle; and
   a display processor configured to display lines connecting points on opposite sides of the heart chamber and the shape of accumulated change in the positions of the lines in the same locations in relation to a static reference in which the lines were first detected after at least a portion of a cardiac cycle as an indicator of asynchronicity.

9. The ultrasonic diagnostic imaging system of claim 8, wherein the display processor further comprises a display processor configured to display in different colors the accumulated change in the positions of lines between points on opposite sides of the heart chamber.

10. The ultrasonic diagnostic imaging system of claim 8, further comprising a scan converter configured for scan converting ultrasonic image data into a desired display format,
    wherein the speckle tracker is configured to track changes in the positions of the points in image data prior to scan conversion.

11. The method of claim 1, wherein tracking further comprises tracking the reference points during the sequence of phases of the heart cycle by feature tracking.

12. The method of claim 1, wherein tracking further comprises tracking the reference points during the sequence of phases of the heart cycle by texture tracking.

13. The ultrasonic diagnostic imaging system of claim 8, wherein the border detector comprises a manual user input by which points are manually placed on opposite sides of a heart chamber in the ultrasound image.

14. A method for depicting the synchronous functioning of the heart from a sequence of images acquired during a portion of the heart cycle comprising:

acquiring a sequence of ultrasound images of the heart with an ultrasound imaging system during a sequence of phases of the heart cycle;
identifying in an image the locations of reference points on heart tissue around a chamber of the heart;
connecting successive pairs of reference points;
tracking the reference points and the connections during the sequence of phases of the heart cycle; and
displaying motion of the reference points during the selected phase or phases of the heart cycle,
wherein connecting further comprises producing lines between successive pairs of reference points along the myocardium; and further comprising:
accumulating positional changes of the lines in the same locations in relation to a static reference in which the lines were first detected during the sequence of phases of the heart cycle; and
wherein displaying further comprises displaying the shape of the accumulated changes of the positions of the lines after the end of the sequence of phases of the heart cycle as an indicator of asynchronicity.

15. The method of claim 14, wherein displaying further comprises displaying the accumulated changes of the positions of the lines in different colors.

16. The method of claim 14, wherein tracking further comprises tracking the reference points during the selected phase or phases of the heart cycle by speckle tracking.

* * * * *